US007601360B2

(12) United States Patent
Breton et al.

(10) Patent No.: US 7,601,360 B2
(45) Date of Patent: *Oct. 13, 2009

(54) EXCITATORY AMINO ACID INHIBITORS FOR TREATING SENSITIVE SKINS

(75) Inventors: Lionel Breton, Versailles (FR); Isabelle Nonotte, Paris (FR)

(73) Assignee: L'Oreal, Paris (FR)

( * ) Notice: Subject to any disclaimer, the term of this patent is extended or adjusted under 35 U.S.C. 154(b) by 290 days.

This patent is subject to a terminal disclaimer.

(21) Appl. No.: 10/401,685

(22) Filed: Mar. 31, 2003

(65) Prior Publication Data

US 2003/0202994 A1    Oct. 30, 2003

Related U.S. Application Data

(63) Continuation of application No. 09/160,151, filed on Sep. 25, 1998, now Pat. No. 6,616,933.

(30) Foreign Application Priority Data

Sep. 25, 1997   (FR) .................................. 97 11959

(51) Int. Cl.
| A61K 9/00 | (2006.01) |
| A61K 8/00 | (2006.01) |
| A61K 31/66 | (2006.01) |
| A61K 31/54 | (2006.01) |
| A61K 31/425 | (2006.01) |
| A61K 31/40 | (2006.01) |

(52) U.S. Cl. .................... 424/400; 514/120; 514/223.3; 514/367; 514/423

(58) Field of Classification Search ................. 424/401, 424/400; 514/120, 223.2, 367, 423
See application file for complete search history.

(56) References Cited

U.S. PATENT DOCUMENTS

| 5,455,042 A | 10/1995 | Sakai et al. |
| 5,607,980 A | 3/1997 | McAtee et al. |
| 5,679,360 A | 10/1997 | de Lacharriere et al. |
| 5,817,699 A | 10/1998 | Flores et al. |
| 6,190,691 B1 * | 2/2001 | Mak ........................... 424/449 |
| 6,203,803 B1 | 3/2001 | de Lacharriere et al. |
| 6,616,933 B1 * | 9/2003 | Breton et al. ............... 424/401 |

FOREIGN PATENT DOCUMENTS

| EP | 0529636 | 3/1993 |
| EP | 0680749 | 11/1995 |
| EP | 0691126 | 1/1996 |
| EP | 0717997 | 6/1996 |
| WO | 92/17168 | 10/1992 |
| WO | 97/10815 | 3/1997 |

OTHER PUBLICATIONS

Xu et al. "Systemic excitatory amino acid receptor antagonists of teh alpha-amino-3-hydroxy-5-methyl-4-isooxazolepropionic acid (AMPA) receptor and the N-methyl-D-aspartate (NMDA) receptor relievemechanical hypersensitivity after transient spinal cod ischemia in rats," Journal of Pharmacology and Experimental Therapeutics, 1993, 267(1), 140-4.*
Johansen et al. "Interactions among GYKI-52466, cyclothiazide, ānd aniracetam at recombinant AMPA and Kainnate receptors," Molecular Pharmacology, 1995, vol. 48, No. 5, pp. 946-955.*
Chen et al. "Contemporary Management of Neuropathic Pain for the primary care physician," Mayo Clin. Proc. 2004, vol. 79, No. 12,, pp. 1533-1545.*
Smullin et al, Interactions between substance P, calcitonin gene-related peptide, taurine and excitatory amino acids in the spinal cord, *Pain*, vol. 42, pp. 93-101 (1990), published by Elsevier Science Publishers B.V., Amsterdam.
*Chemical Abstracts*, vol. 122, No. 19, p. 93, May 8, 1995, Abstract No. 230656k, published by American Chemical Society, Columbus, Ohio.
*Chemical Abstracts*, vol. 119, No. 3, p. 75, Jul. 19, 1993, Abstract No. 20398q, published by American Chemical Society, Columbus, Ohio.
"Excitatory Amino Acid Uptake Inhibitors", http://www.komabiotech.co.kr/product/neuro/category/Excitatory_Amino_Acid.htm, Apr. 4, 2006.
Mennini et al., "Substrate inhibitors and blockers of excitatory amino acid transporters in the treatment of neurodegeneration: critical considerations", European Journal of Pharmacology 479 (2003) 291-296, Elsevier B.V., The Netherlands.
Dana Giulian et al., "Study of Receptor-Mediated Neurotoxins Released by HIV-1-Infected Mononuclear Phagocytes Found in Human Brain", The Journal of Neuroscience, May 15, 1996, 16(10): 3139-3153, The Society for Neuroscience, Washington, DC.
Bong et al., "Spinal Cord Adenosine Receptor Stimulation in Rats Inhibits Peripheral Neutrophil Accumulation", J. Clin. Invest., vol. 98, No. 12, 2779-2785, 1996, American Society for Clinical Investigation Inc., United States.

* cited by examiner

*Primary Examiner*—Shengjun Wang
(74) *Attorney, Agent, or Firm*—Buchanan, Ingersoll & Rooney P.C.

(57) ABSTRACT

Sensitive human skin/scalp/mucous membrane conditions, for example skin irritation and/or dry patches and/or erythemas and/or dysaesthesic sensations and/or sensations of heating and/or pruritus, are therapeutically treated by topically applying thereto an effective condition-alleviating amount of at least one inhibitor of at least one excitatory amino acid.

28 Claims, No Drawings

EXCITATORY AMINO ACID INHIBITORS FOR TREATING SENSITIVE SKINS

CROSS-REFERENCE TO RELATED AND PRIORITY APPLICATIONS

This application is a continuation of application Ser. No. 09/160,151, filed Sep. 25, 1998, now U.S. Pat. No. 6,616,933 incorporated by reference herein in its entirety and relied upon, which claims priority under 35 U.S.C. §119 of FR-97/11959, filed Sep. 25, 1997, assigned to the assignee hereof and expressly incorporated by reference.

BACKGROUND OF THE INVENTION

1. Technical Field of the Invention

The present invention relates to cosmetic/dermatological compositions comprising at least one inhibitor of at least one excitatory amino acid, such as at least one aspartate or glutamate, for the treatment of sensitive human skin, for example the scalp, the area around the eyes and the mucous membranes.

2. Description of the Prior Art

It is known to this art that certain skin types are more sensitive than others. The symptoms of "sensitive skin" were hitherto poorly characterized and the problem of these skin types was consequently poorly defined; what process was involved in skin sensitivity was unknown. Certain researchers believed that sensitive skin was skin which reacted to cosmetic products, while others considered it was skin which reacted to a variety of external factors, not necessarily associated with cosmetic products.

Certain tests have now been developed in an attempt to characterize sensitive skin, for example tests utilizing lactic acid and DMSO which are known irritants. See, for example, the article by K. Lammintausta et al., *Dermatoses*, 36, pages 45-49 (1988); and the article by T. Agner and J. Serup, *Clinical and Experimental Dermatology*, 14, pages 214-217 (1989). However, these tests for characterizing sensitive skin were less than completely successful.

Moreover, sensitive skin was likened to allergic skin.

Since the characteristics of sensitive skin were not well known, it was hitherto very difficult to treat such skin types, and these were treated indirectly, for example by limiting application to the skin of products of irritant nature, such as surfactants, preservatives or fragrances as well as certain active agents, these typically being formulated into a variety of cosmetic compositions.

Many clinical tests have been carried out by the assignee hereof to determine the symptoms associated with sensitive skin. These symptoms are, in particular, subjective signs, which are essentially dysaesthesic sensations. By the term "dysaesthesic sensations" is intended the more or less painful sensations experienced in a particular region of skin, such as stinging, tingling, itching or pruritus, burning, heating, discomfort, tautness, etc.

The assignee hereof has also been able to demonstrate that sensitive skin is not allergic skin. The essential characteristic of sensitive skin is believed to be a mechanism of response to external factors, which can affect any individual, although individuals with so-called "sensitive" skin react faster thereto than others. This mechanism is not immunological.

Thus, the assignee hereof has now found that sensitive skin can be divided into two major clinical forms: irritable and/or reactive skin and intolerant skin.

Irritable and/or reactive skin is a skin which reacts by pruritus, i.e. by itching or stinging, to various factors or challenges such as the environment, emotions, foods, the wind, rubbing, shaving, soap, surfactants, hard water having a high calcium concentration, temperature variations, wool, etc. In general, these signs are associated with dry skin or with skin afflicted with erythema.

Intolerant skin is a skin which reacts, by sensations of heating, tautness, tingling and/or redness, to various factors and challenges such as the environment, emotions, foods, etc. In general, these signs are associated with hyperseborrhoeic or acneic skin, and with erythema.

"Sensitive" scalps have a more univocal clinical semeiology: the sensations of pruritus and/or of stinging and/or heating are essentially triggered by local factors such as rubbing, soap, surfactants, hard water having a high calcium concentration, shampoos or lotions, permanent-wave products, and the like. These sensations are also sometimes triggered by factors such as the environment, emotions and/or foods. Erythema and hyperseborrhoea of the scalp and the presence of dandruff are often associated with the above signs.

Moreover, in certain anatomical regions such as the major folds (groin, genital, axillary, popliteal, anal and submammary regions and in the crook of the elbow) and the feet, sensitive skin is reflected in pruriginous sensations and/or dysaesthesic sensations (heating, stinging) associated in particular with sweat, rubbing, wool, surfactants, hard water having a high calcium concentration and/or temperature variations.

In order to determine whether skin is sensitive or not, a test has also been developed by the assignee hereof. After having carried out a large number of tests for the purpose of defining sensitive skin, it has surprisingly been found that there is a relationship between individuals with sensitive skin and those who react to topical application of capsaicin.

The capsaicin test entails applying 0.05 ml of a cream containing 0.075% capsaicin to about 4 $cm^2$ of skin and in noting the appearance of subjective signs caused by this application, such as stinging, burning and itching. In individuals with sensitive skin, these signs appear between 3 and 20 minutes after topical application and are followed by the appearance of an erythema which begins at the periphery of the zone of application.

Capsaicin causes, in particular, a release of neuropeptides, and in particular tachykinins which originate from sensitive nerve endings in the epidermis and the dermis. It has been observed that the physiopathological schema common to all the sensitive skin conditions is associated with a large capacity to release tachykinins and more particularly substance P into the skin. The dysaesthesic manifestations which are caused by the release of neuropeptides are referred to as "neurogenic".

Substance P is a polypeptide which is produced and released by sensitive nerve endings. It induces, in particular, a degranulation of mastocytes, effecting the release of serotonin and a cascade of biochemical events resulting in an inflammatory reaction. The release of substance P by sensitive nerve endings can be controlled by various active agents including excitatory amino acids such as glutamate and/or aspartate.

SUMMARY OF THE INVENTION

It has now unexpectedly been determined that nerve fibers present in the epidermis and/or the dermis contain excitatory amino acids such as aspartate and/or glutamate, and, thus, that the release of aspartate and/or glutamate close to sensitive nerve endings activates the release of substance P and, hence, the cascade of biochemical events which results in the more or less pronounced nociceptive reactions.

Accordingly, administration of an inhibitor of at least one excitatory amino acid elicits a preventive and/or curative effect on sensitive skin since, by decreasing the release and/or synthesis of excitatory amino acids by nerve fibers and/or by decreasing their binding, the activity attributed to these excitatory amino acids is reduced.

DETAILED DESCRIPTION OF BEST MODE AND SPECIFIC/PREFERRED EMBODIMENTS OF THE INVENTION

More particularly according to the present invention, inhibitors of at least one excitatory amino acid are administered for the treatment of sensitive skin. Indeed, it has now been observed, surprisingly, that the formulation of an inhibitor of at least one excitatory amino acid into a cosmetic or dermatological composition makes it possible to avoid irritation and/or dysaesthesic sensations and/or pruritus in the skin.

The present invention thus features the formulation of at least one inhibitor of at least one excitatory amino acid into cosmetic/dermatological compositions including a physiologically acceptable medium (vehicle, diluent or carrier), for treating sensitive skin.

This invention also features at least one inhibitor of at least one excitatory amino acid formulated into a cosmetic/dermatological composition containing a physiologically acceptable medium, to prevent and/or combat skin irritation and/or dry patches and/or sensations of heating and/or dysaesthesic sensations and/or pruritus in the skin.

In summary, the present invention features formulating at least one inhibitor of at least one excitatory amino acid into a cosmetic/dermatological composition containing a physiologically acceptable medium, to treat skin symptoms associated with the release and/or synthesis and/or binding of at least one excitatory amino acid.

By "physiologically acceptable medium" is intended a cosmetically or dermatologically acceptable medium, which is compatible with the skin, mucous membranes, the nails and the hair. In particular, the composition containing an inhibitor of at least one excitatory amino acid can be topically applied to the face, the neck, the hair and the nails, or to any other area of body skin.

For a substance or substrate to be recognized as an inhibitor of at least one excitatory amino acid, it must inhibit the release and/or binding and/or synthesis of at least one excitatory amino acid, such as glutamate and/or aspartate, in the dermis and/or the epidermis. It must, more particularly, satisfy at least one of the following characteristics:

(a) have pharmacological activity, measured in particular by electrophoresis, such as being a receptor antagonist to one of the receptors of at least one excitatory amino acid, in particular receptors such as AMPA (L-α-amino-3-hydroxy-5-methyl-4-isoxazole propionate), NMDA (N-methyl-D-aspartate) or kainate (the pharmacology and localization make it possible to differentiate these receptors, all three of which are coupled to an ion channel);

(b) lower the extravasation of plasma, measured in particular by the Evans Blue method, observed after antidromic stimulation of the saphene nerve or after stimulation with capsaicin;

(c) lower the cellular cytotoxicity induced on neuronal cell lines after incubation with high concentrations of glutamate.

The clinical signs of sensitive skin are essentially subjective, namely: stinging, tingling, itching or pruritus, tautness, heating. These are occasionally accompanied by erythema. These signs are due to aspecific external factors.

According to the invention, one or more inhibitors of at least one excitatory amino acid can be administered.

Thus, inhibitors of at least one excitatory amino acid include molecules from chemical synthesis and also extracts of animal, plant or bacterial origin.

Exemplary inhibitors of at least one excitatory amino acid include, in particular, ketamine, memantine, (±)-2-amino-3-phosphonopropionic acid, (±)-2-amino-4-phosphonobutyric acid, (±)-2-amino-5-phosphonopentanoic acid, D-8-glutamylaminomethanesulfonic acid, 1,2,3,6,7,8-hexahydro-3-(hydroxyimino)-N,N,7-trimethyl-2-oxobenzo[2,1-b:3,4-c']dipyrrole-5-sulfonamide hydrochloride (referred to more commonly as: NS 257, HCl), cyclothiazide, aniracetam and riluzole.

Preferably, the inhibitor of at least one excitatory amino acid is aniracetam or ketamine.

The amount of inhibitor of the excitatory amino acid in a composition of the invention varies over a wide range, in particular depending on the inhibitory power of the compound and on the desired effect.

To provide an order of magnitude, in the compositions according to the invention, the amount of the inhibitor of at least one excitatory amino acid preferably ranges from 0.000001% to 5% of the total weight of the composition, and more preferably ranges from 0.0001% to 1%.

The compositions according to the invention can be formulated in any pharmaceutical form normally provided for topical application to the skin, in particular formulated as solutions or dispersions of lotion or serum type, emulsions of liquid or semi-liquid consistency of the milk type, obtained by dispersion of a fatty phase in an aqueous phase (O/W) or, conversely, (W/O), or suspensions or emulsions of soft consistency of the aqueous or anhydrous cream or gel type, or, alternatively, microgranules, nanoparticles, microemulsions, nanocapsules, or vesicle dispersions of ionic and/or nonionic type. These compositions are formulated according to the usual techniques.

The subject compositions can also be applied onto the hair in the form of aqueous, alcoholic or aqueous-alcoholic solutions, or in the form of creams, gels, emulsions or mousses or, alternatively, in the form of aerosol compositions containing a propellant under pressure.

The amounts of the various constituents of the compositions according to the invention are those conventionally employed in the fields under consideration.

The compositions of the invention in particular constitute a cleansing, protective, treatment or care cream for the face, for the hands, for the feet, for the major anatomical folds or for the body (for example day creams, night creams, makeup-removing creams, foundation creams, antisun (sunscreen) creams), fluid foundations, makeup-removing milks, protective or care body milks, antisun (sunscreen) milks, skincare lotions, gels or mousses, as cleansing lotions, antisun (sunscreen) lotions, artificial tanning lotions, bath compositions, deodorizing compositions containing a bactericidal agent, aftershave lotions or gels, hair-removing creams, compositions to combat insect bites and analgesic compositions.

The compositions of this invention can also be formulated as a solid preparation constituting a cleansing bar or a soap.

The inhibitor of at least one excitatory amino acid can also be incorporated into any haircare compositions, and in particular shampoos, hair setting lotions, treating lotions, styling creams or gels, dye compositions (in particular oxidation dye compositions) optionally in the form of coloring shampoos, hair-restructuring lotions, permanent-waving compositions (in particular compositions for the first stage of a permanent-waving operation), lotions or gels for preventing hair loss, and the like.

The compositions of the invention can also be formulated for dentibuccal use, for example in the form of a toothpaste. In this case, the composition can contain adjuvants and additives that are typical for compositions for oral use and in particular surfactants, thickeners, wetting agents, polishing agents such as silica, various active ingredients such a fluorides, in particular sodium fluoride, and optionally sweeteners such as sodium saccharinate.

When the composition of the invention is an emulsion, the proportion of the fatty phase advantageously ranges from 5% to 80% by weight, and preferably from 5% to 50% by weight, relative to the total weight of the composition. The oils, the emulsifiers and the coemulsifiers used are those conventional in the particular field. The emulsifier and the coemulsifier are typically present in the subject compositions in a proportion ranging from 0.3% to 30% by weight, and preferably from 0.5 to 30% by weight, relative to the total weight of the composition. The emulsion can also contain lipid vesicles.

In known fashion, the compositions of the invention can also contain adjuvants and additives that are common in the field under consideration, such as hydrophilic or lipophilic gelling agents, hydrophilic or lipophilic active agents, preservatives, antioxidants, solvents, fragrances, fillers, screening agents, dyestuffs and colorants. The amounts of these various adjuvants and additives are those conventional in the particular field, and, for example, range from 0.01% to 10% of the total weight of the composition. Depending on their nature, these adjuvants and additives can be introduced into the fatty phase, into the aqueous phase and/or into the lipid spherules.

Exemplary oils according to the invention, include mineral oils (liquid petroleum jelly), plant oils (liquid fraction of karite butter, sunflower oil), animal oils (perhydrosqualene), synthetic oils (purcellin oil), silicone oils (cyclomethicone) and fluoro oils (perfluoropolyethers). Fatty alcohols and fatty acids (stearic acid) can be added to these oils.

Exemplary emulsifiers suitable for incorporation according to the invention include glyceryl stearate, polysorbate 60 and the mixture PEG-6/PEG-32/glycol stearate marketed under the trademark Tefose®63 by Gattefosse.

Representative solvents which can be used include the lower alcohols, in particular ethanol and isopropanol.

Exemplary hydrophilic gelling agents include carboxyvinyl polymers (carbomer), acrylic copolymers such as acrylate/alkylacrylate copolymers, polyacrylamides, polysaccharides such as hydroxypropyl-cellulose, natural gums and clays, and, exemplary lipophilic gelling agents include modified clays such as bentones, metal salts of fatty acids such as aluminum stearates, and hydrophobic silica.

Exemplary hydrophilic active agents are proteins or protein hydrolysates, amino acids, polyols, urea, allantoin, sugars and sugar derivatives, vitamins and hydroxy acids.

And exemplary ipophilic active agents are retinol (vitamin A) and derivatives thereof, tocopherol (vitamin E) and derivatives thereof, essential fatty acids, ceramides, essential oils and salicylic acid and derivatives thereof.

The inhibitor of at least one excitatory amino acid can, inter alia, be administered in combination with active agents intended, in particular, for the prevention and/or treatment of skin conditions and afflictions.

Exemplary such active agents include:

(a) agents which modify skin differentiation and/or proliferation and/or pigmentation, such as retinoic acid and isomers thereof, retinol and its esters, vitamin D and derivatives thereof, estrogens such as estradiol, kojic acid or hydroquinone;

(b) antibacterial agents such as clindamycin phosphate, erythromycin or antibiotics of the tetracycline family;

(c) antiparasitic agents, in particular metronidazole, crotamiton or pyrethroids;

(d) antifungal agents, in particular compounds belonging to the imidazole family such as econazole, ketoconazole or miconazole or salts thereof, polyene compounds, such as amphotericin B, compounds of the allylamine family such as terbinafine;

(e) steroidal anti-inflammatory agents, such as hydrocortisone, betamethasone valerate or clobetasol propionate, or nonsteroidal anti-inflammatory agents, such as ibuprofen and its salts, diclofenac and its salts, acetylsalicylic acid, acetaminophen or glycyrrhetinic acid;

(f) anaesthetics such as lidocaine hydrochloride and derivatives thereof;

(g) antipruriginous agents such as thenaldine or trimeprazine;

(h) antiviral agents such as acyclovir;

(i) keratolytic agents such as alpha- and beta-hydroxycarboxylic acids or beta-ketocarboxylic acids, their salts, amides or esters and more particularly hydroxy acids such as glycolic acid, lactic acid, salicylic acid, citric acid and fruit acids in general, and $C_2$-$C_{22}$ alkyl derivatives of salicylic acid such as 5-n-octanoylsalicylic acid;

(j) anti-free-radical agents, such as alpha-tocopherol or its esters, superoxide dismutases, certain metal-chelating agents or ascorbic acid and its esters;

(k) antiseborrhoeic agents such as progesterone;

(l) antidandruff agents such as octopirox or zinc pyrithione;

(m) antiacne agents such as retinoic acid or benzoyl peroxide.

The present invention also features a cosmetic or dermatological regime or regimen comprising topically applying a composition as described above containing at least one inhibitor of at least one excitatory amino acid, formulated into a cosmetically or dermatologically acceptable medium, onto the skin, the hair and/or mucous membranes, more particularly of human beings.

More particularly, the subject compositions are topically applied onto sensitive skin and/or onto sensitive scalps.

As indicated hereinabove, sensitive skin is irritable skin. The skin irritation can have many causes. These can be intrinsic causes, associated with deregulation of the physiological mechanisms providing a normal skin. However, these can also be extrinsic causes such as irritant compounds coming into contact with the skin.

Thus, the regime or regimen according to the invention is well suited for reducing skin irritation.

This treatment can be carried out, in particular, by topically applying the composition according to any conventional technique. For example: application to the skin or mucous membranes of a cream, a gel, a serum, a lotion, a makeup-removing milk, an antisun (sunscreen) composition, or application to wet or dry hair of shampoos or conditioners, or application of toothpaste to the gums.

Thus, advantageously, the inhibitor of at least one excitatory amino acid is administered in combination with active agents having a skin-irritating side effect, which are common in the fields under consideration. The presence of this inhibitor of at least one excitatory amino acid in a composition of the invention containing an active agent eliciting an irritant effect makes it possible to attenuate this irritant effect greatly, or even to completely eliminate it.

Thus, the present invention also features cosmetic or dermatological compositions containing a physiologically acceptable medium (diluent, vehicle or carrier) and at least one active agent exhibiting an irritant side effect, such compositions also comprising at least one inhibitor of at least one excitatory amino acid.

Especially representative skin-irritating active agents/species include α-hydroxy acids (fruit acids), β-hydroxy acids such as salicylic acid and alkyl derivatives thereof, α-keto acids, β-keto acids, retinoids, anthralins, anthranoids, peroxides, lithium salts, antimetabolites and vitamin D and derivatives thereof.

In order to further illustrate the present invention and the advantages thereof, the following specific examples are given, it being understood that same are intended only as illustrative and in nowise limitative.

In said examples to follow, all parts and percentages are given by weight. Also in said examples to follow, each of which relates to a specific composition according to the invention, and each such composition was formulated by simply intimately admixing the various constituents thereof.

EXAMPLE 1

| Makeup-removing lotion for the face: | | |
|---|---|---|
| Aniracetam | | 0.0001 |
| Antioxidant | | 0.05 |
| Isopropanol | | 40.00 |
| Preservative | | 0.30 |
| Water | qs | 100% |

EXAMPLE 2

| Care gel for the face: | | |
|---|---|---|
| Aniracetam | | 0.05 |
| Hydroxypropylcellulose (Klucel H marketed by Hercules) | | 1.00 |
| Antioxidant | | 0.05 |
| Isopropanol | | 30.00 |
| Preservative | | 0.30 |
| Water | qs | 100% |

EXAMPLE 3

| Dermatological care cream for the face (oil-in-water emulsion): | | |
|---|---|---|
| Ketamine | | 0.002 |
| Glyceryl stearate | | 2.00 |
| Polysorbate 60 (Tween 60 marketed by ICI) | | 1.00 |
| Stearic acid | | 1.40 |
| Triethanolamine | | 0.70 |
| Carbomer | | 0.40 |
| Liquid fraction of karite butter | | 12.00 |
| Perhydrosqualene | | 12.00 |
| Antioxidant | | 0.05 |
| Fragrance | | 0.5 |
| Preservative | | 0.30 |
| Water | qs | 100% |

EXAMPLE 4

| Anti-wrinkle care cream for the face (oil-in-water emulsion): | | |
|---|---|---|
| Aniracetam | | 0.15 |
| Glyceryl stearate | | 2.00 |
| Polysorbate 60 (Tween 60 marketed by ICI) | | 1.00 |
| Stearic acid | | 1.40 |
| 5-n-Octanoylsalicylic acid | | 0.50 |
| Triethanolamine | | 0.70 |
| Carbomer | | 0.40 |
| Liquid fraction of karite butter | | 12.00 |
| Perhydrosqualene | | 12.00 |
| Antioxidant | | 0.05 |
| Fragrance | | 0.5 |
| Preservative | | 0.30 |
| Water | qs | 100% |

EXAMPLE 5

| Shampoo: | | |
|---|---|---|
| Aniracetam | | 0.0001 |
| Sodium magnesium lauryl ether sulfate containing 4 mol of ethylene oxide, marketed under the trademark Texapon ASV by Henkel (anionic surfactant) | | 6.5 g |
| Hydroxypropylcellulose (Klucel H marketed by Hercules) | | 1.00 |
| Fragrance | | 0.50 |
| Preservative | | 0.30 |
| Water | qs | 100% |

EXAMPLE 6

| Emulsified gel for treating insect bites (oil-in-water emulsion): | | |
|---|---|---|
| Memantine | | 0.01 |
| Purcellin oil (marketed by Dragocco) | | 7.00 |
| PEG-6/PEG-32/glycol stearate (Tefose ® 63 marketed by Gattefosse) | | 0.30 |
| Sumatriptan | | 0.02 |
| Preservative | | 0.30 |
| Fragrance | | 0.40 |

-continued

Emulsified gel for treating insect bites (oil-in-water emulsion):

| | | |
|---|---|---|
| Carbomer | | 0.60 |
| Crotamiton | | 5.00 |
| Glycyrrhetinic acid | | 2.00 |
| Ethyl alcohol | | 5.00 |
| Triethanolamine | | 0.20 |
| Water | qs | 100% |

EXAMPLE 7

Rosacea dermatological treatment cream for the face (oil-in-water emulsion):

| | | |
|---|---|---|
| Ketamine | | 0.025 |
| Glyceryl stearate | | 2.00 |
| Polysorbate 60 (Tween 60 marketed by ICI) | | 1.00 |
| Stearic acid | | 1.40 |
| Metronidazole | | 1.00 |
| Triethanolamine | | 0.70 |
| Carbomer | | 0.40 |
| Liquid fraction of karite butter | | 12.00 |
| Liquid petroleum jelly | | 12.00 |
| Antioxidant | | 0.05 |
| Fragrance | | 0.5 |
| Preservative | | 0.30 |
| Water | qs | 100% |

EXAMPLE 8

Cream for treating sensitive skin against solar erythema (oil-in-water emulsion):

| | | |
|---|---|---|
| Aniracetam | | 0.025 |
| Glyceryl stearate | | 2.00 |
| Polysorbate 60 (Tween 60 marketed by ICI) | | 1.00 |
| Stearic acid | | 1.40 |
| Glycyrrhetinic acid | | 2.00 |
| Triethanolamine | | 0.70 |
| Carbomer | | 0.40 |
| Liquid fraction of karite butter | | 12.00 |
| Sunflower oil | | 10.00 |
| Antioxidant | | 0.05 |
| Fragrance | | 0.5 |
| Preservative | | 0.30 |
| Water | qs | 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for treating dysaesthesic sensations of sensitive skin or scalp in an individual, where said dysaesthesic sensations result only from at least one factor or challenge selected from the group consisting of: rubbing, shaving, soap, surfactants, hard water having a high calcium concentration, temperature variations, wool, foods, the wind, the environment and emotions, said method comprising:

decreasing the release, synthesis or binding of an aspartate or glutamate excitatory amino acid by nerve fibers in the epidermis or dermis of said individual having sensitive skin or scalp by topically applying to said sensitive skin or scalp of said individual, a cosmetic or dermatological composition comprising at least one inhibitor of said aspartate or glutamate excitatory amino acid selected from the group consisting of memantine, (±)-2-amino-3-phosphonopropionic acid, (±)-2-amino-4-phosphonobutyric acid, (±)-2-amino-5-phosphonopentanoic acid, D-γ-glutamylaminomethanesulfonic acid, 1,2,3,6,7,8-hexahydro-3-(hydroxyamino)-N,N,7-trimethyl-2-oxobenzo[2,1-b:3,4-c']dipyrrole-5-sulfonamide hydrochloride (NS 257, HC1), aniracetam, riluzole, and mixtures thereof in an amount effective to treat dysaesthesic sensations of said sensitive skin or scalp, formulated into a physiologically acceptable medium therefor wherein said sensitive skin is determined to be sensitive by applying 0.05 ml of a cream containing 0.075% capsaicin to about 4 $cm^2$ of skin and said application of capsaicin results in the appearance of subjective signs caused by this application, such as stinging, burning and itching, where these signs appear between 3 and 20 minutes after topical application and are followed by the appearance of an erythema which begins at the periphery of the zone of application.

2. The method according to claim 1, wherein said sensitive skin is irritable or reactive skin.

3. The method according to claim 1, wherein said sensitive skin is intolerant skin.

4. The method according to claim 1, wherein said dysaesthesic sensations are selected from the group consisting of stinging, tingling, itching, pruritus, heating, discomfort, tautness and erythema.

5. The method according to claim 2, wherein said dysaesthesic sensations are selected from the group consisting of stinging, tingling, itching, pruritus, heating, discomfort, tautness and erythema.

6. The method according to claim 3, wherein said dysaesthesic sensations are selected from the group consisting of stinging, tingling, itching, pruritus, heating, discomfort, tautness and erythema.

7. The method according to claim 1, wherein said physiologically acceptable medium is selected from the group consisting of an aqueous solution, an aqueous-alcoholic solution, a water-in-oil emulsion, an oil-in-water emulsion, a microemulsion, an aqueous gel, an anhydrous gel, a serum, and a vesicle dispersion.

8. The method according to claim 1, wherein said at least one inhibitor is applied in an amount ranging from 0.00001 to 5% by weight relative to the total weight of the composition.

9. The method according to claim 1, wherein said at least one inhibitor is applied in an amount ranging from 0.0001 to 1% by weight relative to the total weight of the composition.

10. The method according to claim 1, wherein said composition further comprises at least one agent selected from the group consisting of an antibacterial agent, antiparasitic agent, antifungal agent, anti-inflammatory agent, anti-pruriginous agent, anaesthetic, antiviral agent, keratolytic agent, anti-free-radical agent, anti-seborrhoeic agent, antidandruff agent, antiacne agent, an agent which modifies skin differentiation, an agent which modifies skin proliferation, and an agent which modifies skin pigmentation.

11. A method for treating dysaesthesic sensations of sensitive skin or scalp in an individual, where said dysaesthesic sensations result only from at least one factor or challenge selected from the group consisting of: rubbing, shaving, soap, surfactants, hard water having a high calcium concentration, temperature variations, wool, foods, the wind, the environment and emotions, said method comprising:

decreasing the release, synthesis or binding of an aspartate or glutamate excitatory amino acid by nerve fibers in the epidermis or dermis of said individual having sensitive skin or scalp by topically applying to said sensitive skin or scalp of said individual, a cosmetic or dermatological composition comprising at least one active agent having an irritant side effect, in an amount effective to cause irritation of said sensitive skin or scalp, and at least one inhibitor of said aspartate or glutamate excitatory amino acid, in an amount effective to attenuate or eliminate said irritation, formulated into a physiologically acceptable medium therefor, said at least one inhibitor being selected from the group consisting of memantine, (±)-2-amino-3-phosphonopropionic acid, (±)-2-amino-4-phosphonobutyric acid, (±)-2-amino-5-phosphonopentanoic acid, D-γ-glutamylaminomethanesulfonic acid, 1,2,3,6,7,8-hexahydro-3-(hydroxyimino)-N,N,7-trimethyl-2-oxobenzo[2,1-b:3,4-c']dipyrrole-5-sulfonamide hydrochloride (NS 257, HC1), aniracetam, riluzole, and mixtures thereof;

wherein said sensitive skin is determined to be sensitive by applying 0.05 ml of a cream containing 0.075% capsaicin to about 4 cm$^2$ of skin and said application of capsaicin results in the appearance of subjective signs caused by this application, such as stinging, burning and itching, where these signs appear between 3 and 20 minutes after topical application and are followed by the appearance of an erythema which begins at the periphery of the zone of application.

12. The method according to claim 11, wherein said sensitive skin is irritable or reactive skin.

13. The method according to claim 11, wherein said sensitive skin is intolerant skin.

14. The method according to claim 11, wherein said irritation comprises dysaesthesic sensations selected from the group consisting of stinging, tingling, itching, pruritus, heating, discomfort, tautness and erythema.

15. The method according to claim 12, wherein said irritation comprises dysaesthesic sensations selected from the group consisting of stinging, tingling, itching, pruritus, heating, discomfort, tautness and erythema.

16. The method according to claim 13, wherein said irritation comprises dysaesthesic sensations selected from the group consisting of stinging, tingling, itching, pruritus, heating, discomfort, tautness and erythema.

17. The method according to claim 11, wherein said physiologically acceptable medium is selected from the group consisting of an aqueous solution, an aqueous-alcoholic solution, a water-in-oil emulsion, an oil-in-water emulsion, a microemulsion, an aqueous gel, an anhydrous gel, a serum, and a vesicle dispersion.

18. The method according to claim 11, wherein said at least one inhibitor is applied in an amount ranging from 0.00001 to 5% by weight relative to the total weight of the composition.

19. The method according to claim 11, wherein said at least one inhibitor is applied in an amount ranging from 0.0001 to 1% by weight relative to the total weight of the composition.

20. A method for treating dysaesthesic sensations of sensitive skin or scalp in an individual, where said dysaesthesic sensations result only from at least one factor or challenge selected from the group consisting of: rubbing, shaving, soap, surfactants, hard water having a high calcium concentration, temperature variations, wool, foods, the wind, the environment and emotions, said method comprising:

decreasing the release, synthesis or binding of an aspartate or glutamate excitatory amino acid by nerve fibers in the epidermis or dermis of said individual having sensitive skin or scalp by topically applying to said sensitive skin or scalp of said individual, a cosmetic or dermatological composition comprising at least one active agent having an irritant side effect which is selected from the group consisting of α-hydroxy acids, β-hydroxy acids, α-keto acids, β-keto acids, retinoids, anthralins, anthranoids, peroxides, lithium salts, antimetabolites and vitamin D, in an amount effective to cause irritation of said sensitive skin or scalp, and at least one inhibitor of said aspartate or glutamate excitatory amino acid, in an amount effective to attenuate or eliminate said irritation, formulated into a physiologically acceptable medium therefor, said at least one inhibitor being selected from the group consisting of memantine, (±)-2-amino-3-phosphonopropionic acid, (±)-2-amino-4-phosphonobutyric acid, (±)-2-amino-5-phosphonopentanoic acid, D-γ-glutamylaminomethanesulfonic acid, 1,2,3,6,7,8-hexahydro-3-(hydroxyimino)-N,N,7-trimethyl-2-oxobenzo[2,1-b:3,4-c']dipyrrole-5-sulfonamide hydrochloride (NS 257, HC1), aniracetam, riluzole, and mixtures thereof;

wherein said sensitive skin is determined to be sensitive by applying 0.05 ml of a cream containing 0.075% capsaicin to about 4 cm$^2$ of skin and said application of capsaicin results in the appearance of subjective signs caused by this application, such as stinging, burning and itching, where these signs appear between 3 and 20 minutes after topical application and are followed by the appearance of an erythema which begins at the periphery of the zone of application.

21. The method according to claim 20, wherein said sensitive skin is irritable or reactive skin.

22. The method according to claim 20, wherein said sensitive skin is intolerant skin.

23. The method according to claim 20, wherein said irritation comprises dysaesthesic sensations selected from the group consisting of stinging, tingling, itching, pruritus, heating, discomfort, tautness and erythema.

24. The method according to claim 21, wherein said irritation comprises dysaesthesic sensations selected from the group consisting of stinging, tingling, itching, pruritus, heating, discomfort, tautness and erythema.

25. The method according to claim 22, wherein said irritation comprises dysaesthesic sensations selected from the group consisting of stinging, tingling, itching, pruritus, heating, discomfort, tautness and erythema.

26. The method according to claim 20, wherein said physiologically acceptable medium is selected from the group consisting of an aqueous solution, an aqueous-alcoholic solution, a water-in-oil emulsion, an oil-in-water emulsion, a microemulsion, an aqueous gel, an anhydrous gel, a serum, and a vesicle dispersion.

27. The method according to claim 20, wherein said at least one inhibitor is applied in an amount ranging from 0.00001 to 5% by weight relative to the total weight of the composition.

28. The method according to claim 20, wherein said at least one inhibitor is applied in an amount ranging from 0.0001 to 1% by weight relative to the total weight of the composition.

\* \* \* \* \*